United States Patent
Ye et al.

(10) Patent No.: US 11,084,776 B2
(45) Date of Patent: Aug. 10, 2021

(54) MACROPOROUS CATALYST FOR THE PREPARATION OF ALIPHATIC AMINES

(71) Applicant: RHODIA OPERATIONS, Paris (FR)

(72) Inventors: Shengyin Ye, Shanghai (CN); Javier Diaz-Maroto Carpintero, Shanghai (CN); Fabien Ocampo, La Courneuve (FR); Philippe Leconte, Saint Genis-Laval (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/074,556

(22) PCT Filed: Feb. 4, 2016

(86) PCT No.: PCT/CN2016/073491
§ 371 (c)(1),
(2) Date: Aug. 1, 2018

(87) PCT Pub. No.: WO2017/132938
PCT Pub. Date: Aug. 10, 2017

(65) Prior Publication Data
US 2019/0031596 A1    Jan. 31, 2019

(51) Int. Cl.
| | | |
|---|---|---|
| C07C 209/16 | (2006.01) | |
| B01J 21/04 | (2006.01) | |
| B01J 23/72 | (2006.01) | |
| B01J 23/78 | (2006.01) | |
| B01J 23/889 | (2006.01) | |
| B01J 35/10 | (2006.01) | |
| C07C 211/08 | (2006.01) | |

(52) U.S. Cl.
CPC ............. *C07C 209/16* (2013.01); *B01J 21/04* (2013.01); *B01J 23/72* (2013.01); *B01J 23/78* (2013.01); *B01J 23/889* (2013.01); *B01J 35/1014* (2013.01); *B01J 35/1019* (2013.01); *B01J 35/1038* (2013.01); *B01J 35/1042* (2013.01); *B01J 35/1066* (2013.01); *B01J 2208/00017* (2013.01); *B01J 2523/22* (2013.01); *B01J 2523/25* (2013.01); *B01J 2523/27* (2013.01); *B01J 2523/31* (2013.01); *B01J 2523/37* (2013.01); *B01J 2523/67* (2013.01); *B01J 2523/72* (2013.01); *B01J 2523/842* (2013.01); *B01J 2523/845* (2013.01); *B01J 2523/847* (2013.01); *C07C 211/08* (2013.01)

(58) Field of Classification Search
CPC ... B01J 21/04; B01J 23/72; B01J 23/78; B01J 23/889; B01J 35/1014; B01J 35/1019; B01J 35/1038; B01J 35/1042; B01J 35/1066; B01J 2208/00017; B01J 2523/22; B01J 2523/25; B01J 2523/27; B01J 2523/31; B01J 2523/37; B01J 2523/67; B01J 2523/72; B01J 2523/842; B01J 2523/845; B01J 2523/847; C07C 209/16; C07C 211/08

See application file for complete search history.

(56) References Cited

U.S. PATENT DOCUMENTS

| | | |
|---|---|---|
| 2,915,365 A | 12/1959 | Saussol |
| 3,856,708 A | 12/1974 | Carithers |
| 4,014,933 A | 3/1977 | Boettger et al. |
| 4,138,437 A | 2/1979 | Strauss et al. |
| 4,206,149 A | 6/1980 | Slaugh |
| 4,206,150 A | 6/1980 | Slaugh |
| 4,229,374 A | 10/1980 | Slaugh et al. |
| 4,251,465 A | 2/1981 | Swift et al. |
| 4,293,716 A | 10/1981 | Swift et al. |
| 4,654,440 A | 3/1987 | Card et al. |
| 5,916,838 A | 6/1999 | Wulff-Doring et al. |
| 5,958,825 A | 9/1999 | Wulff-Doring et al. |
| 6,262,259 B1 | 7/2001 | Cotting et al. |
| 2002/0040161 A1 | 4/2002 | Ryan et al. |
| 2007/0087934 A1 | 4/2007 | Martens et al. |
| 2007/0191212 A1 | 8/2007 | Schubert et al. |
| 2007/0232833 A1 | 10/2007 | Haese et al. |
| 2008/0004472 A1 | 1/2008 | Nishimura et al. |
| 2011/0137029 A1* | 6/2011 | Kubanek .................. B01J 23/83 544/106 |
| 2011/0137030 A1 | 6/2011 | Kubanek et al. |
| 2011/0172430 A1 | 7/2011 | Ernst et al. |

(Continued)

FOREIGN PATENT DOCUMENTS

| | | |
|---|---|---|
| CN | 1165712 A | 11/1977 |
| CN | 102781571 A | 11/2012 |
| CN | 103657682 A | 3/2014 |

(Continued)

OTHER PUBLICATIONS

Tan et al. (Riyong Huaxue Gongye / Riyong Huaxue Gongye, 2003, vol. 33, Issue 3, p. 150-152).*

English Translation of Tan et al. (Riyong Huaxue Gongye / Riyong Huaxue Gongye, 2003, vol. 33, Issue 3, p. 150-152).*

(Continued)

*Primary Examiner* — Sudhakar Katakam
*Assistant Examiner* — Jennifer C Sawyer
(74) *Attorney, Agent, or Firm* — Osha Bergman Watanabe & Burton LLP

(57) ABSTRACT

A process for the preparation of aliphatic amines, comprises reacting an aliphatic alcohol with an aminating agent in the presence of a catalyst. The catalyst contains copper oxide on a support made of porous alumina, wherein the porous alumina has a volume, corresponding to pores greater than 500 Å in diameter, of from 10 ml/100 g to 95 ml/100 g.

10 Claims, No Drawings

(56) References Cited

U.S. PATENT DOCUMENTS

2011/0251434 A1   10/2011   Muller et al.

FOREIGN PATENT DOCUMENTS

| EP | 0015801 B1 | 7/1983 |
| EP | 0097539 B1 | 8/1986 |
| GB | 1554516 A | 10/1979 |
| JP | 2007175662 A | 7/2007 |
| JP | 2014043415 A | 3/2014 |

OTHER PUBLICATIONS

Catalytic Aluminas I. Surface Chemistry of Eta and Gamma Alumina; D.S. Maciver, etc.; Journal of Catalysis 2, 485-497; 1963).
The Journal of the American Society, 60, 309 (1938).
Kirk-Othmer Encyclopedia of Chemical Technology, vol. 2, p. 291-297.

* cited by examiner

MACROPOROUS CATALYST FOR THE PREPARATION OF ALIPHATIC AMINES

This application is a U.S. national phase entry under 35 U.S.C. § 371 of International Application No. PCT/CN2016/073491, filed on Feb. 4, 2016. The entire content of this application is explicitly incorporated herein by this reference.

TECHNICAL FIELD

The present invention relates to a process for the preparation of aliphatic amines. The process comprises reacting an aliphatic alcohol with an aminating agent in the presence of a catalyst comprising copper oxide on a support made of porous alumina.

BACKGROUND ART

Aliphatic amines are of considerable industrial importance and find application in almost every filed of modern technology, agriculture and medicine. Aliphatic amines, such as tertiary amines, can be used for as intermediates for disinfectants, foam boosters for household liquid detergents, active agents for hair conditioners, softeners for clothes, reagents for mild dyeing, etc.

Among the various known processes for the preparation of aliphatic amines, one process is one-step amination of aliphatic alcohols, such as long chain fatty alcohols, with various starting amines, such as ammonia, primary and secondary amines. For example, the process may be a reaction of an aliphatic alcohol with a dimethylamine to yield the corresponding alkyldimethylamine. Such reaction is initiated by the dehydrogenation of a starting aliphatic alcohol to the corresponding aldehyde, with the generation of two hydrogens, as shown in the reaction scheme below:

$RCH_2OH \rightarrow RCHO+2H$ (1) dehydrogenation of a starting aliphatic alcohol $RCHO+Me_2NH \rightarrow RCH(OH)NMe_2$ (2) non-catalytic addition of $Me_2NH$ to an aldehyde $RCH(OH)NMe_2+2H \rightarrow RCH_2NMe_2+H_2O$ (3) hydrogenolysis of the adduct to a tertiary amine $RCH(OH)NMe_2 \rightarrow R'CH=CHNMe_2+H_2O$ (4) dehydration of the adduct to form an enamine $R'CH=CHNMe_2+2H \rightarrow RCH_2NMe_2$ (5) hydrogenation of an enamine to a tertiary amine The addition of $Me_2NH$ to the generated aldehyde proceeds non-catalytically to form the corresponding aldehyde-amine adduct, followed by hydrogenolysis of the adduct to the final tertiary amine $RCH_2NMe_2$, with liberation of water or by dehydration of the adduct to form an enamine, which is then hydrogenated to the final $RNMe_2$. Amination of the aliphatic alcohol with a primary amine such as $MeNH_2$ proceeds by the same reaction mechanism to form first the corresponding secondary amine, RNHMe, which reacts again with the starting aliphatic alcohol to form the dialkyl tertiary amine, $R_2NMe$. Amination with ammonia proceeds by a similar stepwise mechanism to form trialkyl amines $R_3N$, via the formation of intermediate $RNH_2$ and $R_2NH$. The reaction scheme shown above suggests that supply of bulk hydrogen is not necessary for the hydrogenolysis step (3) and hydrogenation step (5) because the required hydrogen is generated by the dehydrogenation of the starting aliphatic alcohol. However, the process is preferably carried out in the presence of additional hydrogen gas.

Various catalysts have been studied for processes of the preparation of aliphatic amines by using the one-step amination method, notably copper-containing catalysts. It is known that unsupported elemental copper catalysts can be employed for the one-step amination method. However, one problem is that such catalysts have limited lifetime and a gradual decrease in catalytic activity can be observed over a period of days or weeks. To mitigate such drawback, the catalytic metal, such as copper, can be deposited onto a support which has high surface area and thus has higher activities compared to unsupported counterparts.

It is disclosed in U.S. Pat. No. 4,654,440 that a catalyst containing copper as the catalytic metal, which is supported by gamma-alumina, can be employed for the process of preparing monoalkylamine by using alcohol and ammonia as the starting materials. Notably, gamma-alumina is known to contain mainly pores having a diameter of 40 to 80 Å (angstrom) (ref: Catalytic Aluminas I. Surface Chemistry of Eta and Gamma Alumina; D. S. Maciver, etc.; Journal of Catalysis 2, 485-497; 1963). Also, it is disclosed in U.S. Pat. No. 5,916,838 that a catalyst containing ruthenium, nickel and/or cobalt, which is on a BASF D10-10 alumina support, can be used for amination reactions. It is disclosed that BASF D10-10 alumina has a maximum of distribution of pore diameters in the mesoporosity range at from 80 Å to 500 Å (ref: US patent publication no. 2007/0191212).

For the preparation of the aliphatic amines by using the one-step amination method, it is desired to obtain high conversion rate of the aliphatic alcohols, at the same time, to maintain minimal level of side reactions. For example, in the preparation of alkyldimethylamines by reacting an aliphatic alcohol with a dimethylamine, one significant side reaction is the disproportionation of $Me_2NH$ to $MeNH_2$ and $Me_3N$, which will decrease the yield of the target tertiary amines. It remains a challenge to provide a catalyst which has long lasting activities and which can lead to high efficiency and good selectivity of the reaction.

SUMMARY OF INVENTION

In one aspect of the present invention, there is provided a process of reacting an aliphatic alcohol of formula (I)

$R_1CH_2OH$ (I), wherein $R_1$ is a linear or branched, saturated or unsaturated aliphatic group having from 3 to 21 carbon atoms, with an aminating agent of formula (II)

wherein $R_2$ and $R_3$, the same or different, are hydrogen or a linear or branched, saturated or unsaturated aliphatic group having from 1 to 24 carbon atoms, for obtaining an aliphatic amine of formula (III), (IV) or (V)

-continued

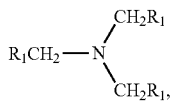
(V)

wherein the reaction is carried out in the presence of a catalyst comprising copper oxide on a support made of porous alumina; wherein the porous alumina has a volume, corresponding to pores greater than 500 Å in diameter, of from 10 ml/100 g to 95 ml/100 g.

Preferably, the porous alumina has a volume, corresponding to pores greater than 500 Å in diameter, of from 20 ml/100 g to 95 ml/100 g.

More preferably, the porous alumina has a volume, corresponding to pores greater than 500 Å in diameter, of from 30 ml/100 g to 95 ml/100 g.

The porous alumina preferably has a specific surface area of from 10 m²/g to 280 m²/g.

More preferably, the porous alumina has a specific surface area of from 50 m²/g to 280 m²/g.

The catalyst may further comprise a compound of at least one element selected from Fe, Co, Zn, Ni, Cr, Mn, Mg, Ba and rare earth metals.

The catalyst may comprise from 5 wt % to 50 wt % of copper oxide, weight percentage based on the total weight of the catalyst.

Notably, the aminating agent has the formula (VI)

(VI)

wherein $R_4$ and $R_5$, the same or different, are a linear or branched, saturated or unsaturated aliphatic group having from 1 to 24 carbon atoms, the aliphatic amine has the formula (VII):

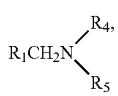
(VII)

wherein $R_1$ is a linear or branched, saturated or unsaturated aliphatic group having from 3 to 21 carbon atoms, $R_4$ and $R_5$ are as defined in formula (VI).

Preferably, the aliphatic alcohol and the aminating agent are mixed together with a flow of hydrogen and the mixture is continuously introduced into a reaction zone, wherein the molar ratio of the aliphatic alcohol/the aminating agent/the hydrogen is in the range of from 1:1:5 to 1:2:20.

More preferably, the molar ratio of the aliphatic alcohol/the aminating agent/the hydrogen is in the range of from 1:1:5 to 1:1.2:15.

The reaction may be carried out at a temperature of from 150° C. to 350° C.

Preferably, the reaction is carried out at a temperature of from 200° C. to 250° C.

The reaction may be carried out under a pressure of from 0 to 5 barg.

Preferably, the reaction is carried out under a pressure of from 0 to 0.5 barg.

In another aspect of the present invention, there is provided a composition comprising:
an aliphatic alcohol of formula (I)

$R_1CH_2OH$     (I),

wherein $R_1$ is a linear or branched, saturated or unsaturated aliphatic group having from 3 to 21 carbon atoms;
an aminating agent of formula (II)

(II)

wherein $R_2$ and $R_3$, the same or different, are hydrogen or a linear or branched, saturated or unsaturated aliphatic group having from 1 to 24 carbon atoms; and
a catalyst comprising copper oxide on a support made of porous alumina; wherein the porous alumina has a volume, corresponding to pores greater than 500 Å in diameter, of from 10 ml/100 g to 95 ml/100 g.

DETAILED DESCRIPTION

Throughout the description, including the claims, the term "comprising one" or "comprising a" should be understood as being synonymous with the term "comprising at least one", unless otherwise specified, "between" and "from . . . to . . . " should be understood as being inclusive of the limits.

As used herein, "weight percent," "wt %," "percent by weight," "% by weight," and variations thereof refer to the concentration of a substance as the weight of that substance divided by the total weight of the composition and multiplied by 100.

In the context of the present invention, the term "macroporosity" refers to pores greater than 500 Å in diameter; the term "mesoporosity" refers to pores greater than 20 Å and less than 500 Å in diameter.

The present invention relates to a process for the preparation of aliphatic amines by reacting an aliphatic alcohol with an aminating agent. The aliphatic alcohols of the invention has the formula (I):

$R_1CH_2OH$     (I)

wherein $R_1$ is a linear or branched, saturated or unsaturated aliphatic group having from 3 to 21 carbon atoms, preferably from 3 to 17 carbon atoms, more preferably, from 7 to 17 carbon atoms.

The aminating agent of the process may be selected from the group consisting of ammonia, primary amines, secondary amines and a mixture thereof. It is appreciated that the aminating agent may be a single species of amine compound or a mixture of more than one amine compounds. The aminating agent of the invention is represented by the formula (II):

(II)

wherein $R_2$ and $R_3$, the same or different, are hydrogen or a linear or branched, saturated or unsaturated aliphatic group having from 1 to 24 carbon atoms, preferably from 1 to 18 carbon atoms, more preferably from 1 to 4 carbon atoms.

The aliphatic amines that are formed herein are represented by the formula (III), (IV) or (V):

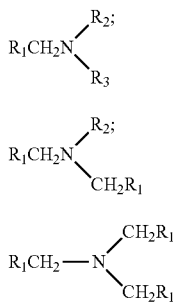

wherein $R_1$, $R_2$ and $R_3$ are as defined above.

Examples of aliphatic alcohols that can be used herein include 1-octanol, 1-decanol, 1-dodecanol, 1-tetradecanol, 1-hexadecanol, 1-octadecanol, 2-ethyl-1-hexanol, oleyl alcohol, 1-nonanol and mixtures thereof.

Primary amines that can be used herein include monomethylamine, monoethylamine, dodecylamine, hexadecylamine, 2-ethylhexylamine and mixtures thereof. Secondary amines that can be used herein include dimethylamine, diethylamine, dodecylmethylamine, dioctylamine and mixtures thereof.

Aliphatic amines that can be prepared herein include octyldimethylamine, octylmonomethylamine, dioctylmethylamine, octylamine, decyldimethylamine, decylmonomethylamine, didecylmethylamine, decylamine, dodecyldimethylamine, dodecylmonomethylamine, didodecylmethylamine, didodecylamine, dodecylamine, 2-ethylhexyldimethylamine, oleyldimethylamine, tetradecyldimethylamine, tetradecylmonomethylamine, ditetradecylmethylamine, tetradecylamine, hexadecyldimethylamine and octadecyldimethylamine.

In one preferred embodiment of the present invention, the aminating agent is a secondary amine having the formula of (VI):

(VI)

wherein $R_4$ and $R_5$, the same or different, are a linear or branched, saturated or unsaturated aliphatic group having from 1 to 24 carbon atoms, preferably from 1 to 18 carbon atoms, more preferably from 1 to 4 carbon atoms. Accordingly, the aliphatic amine that are formed has the formula (VII):

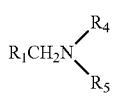
(VII)

wherein $R_1$ is as defined in formula (I), $R_4$ and $R_5$ are as defined in formula (VI).

According to the present invention, the reaction of the aliphatic alcohol and the aminating agent is carried out in the presence of a catalyst comprising copper oxide on a support made of porous alumina; wherein the porous alumina has a volume, corresponding to pores greater than 500 Å in diameter, of from 10 ml/100 g to 95 ml/100 g.

Preferably, the porous alumina has a volume, corresponding to pores greater than 500 Å in diameter, of from 20 ml/100 g to 95 ml/100 g.

More preferably, the porous alumina has a volume, corresponding to pores greater than 500 Å in diameter, of from 30 ml/100 g to 95 ml/100 g.

The porous alumina of the invention notably has a pore size distribution within the macroporosity range. The volume for the pores with a diameter greater than 500 Å represents the cumulative volume created by all the pores with a size greater than a diameter of 500 Å. This volume may be measured by the mercury penetration technique which is well known to a person skilled in the art. The measurement can be conveniently conducted by using a commercially available mercury porosimetry following the instructions of the manufacturer.

The macroporosity is advantageously formed during the process for shaping the particles by the techniques described below, or like, for example, the addition of porogen.

According to one characteristics of the invention, the porous alumina exhibits a total pore volume of from 15 ml/100 g to 120 ml/100 g with a pore volume corresponding to pores greater than 200 Å in diameter of from 15 ml/100 g to 120 ml/100 g. According to another characteristics of the invention, the porous alumina exhibits a total pore volume of from 20 ml/100 g to 150 ml/100 g with a pore volume corresponding to pores greater than 70 Å in diameter of from 20 ml/100 g to 150 ml/100 g. Measurement of such pore volumes can be made by using methods similar to that described above.

Advantageously, the porous alumina of the present invention has a specific surface area of from 10 $m^2/g$ to 280 $m^2/g$, preferably, from 20 $m^2/g$ to 280 $m^2/g$, more preferably, from 50 $m^2/g$ to 280 $m^2/g$.

In the context of the present invention, the specific surface area is notably a BET specific surface area determined by nitrogen adsorption in accordance with ASTM standard D 3663-78 based on the Brunauer-Emmett-Teller method described in the periodical "The Journal of the American Society", 60, 309 (1938).

Preferably, the catalyst of the present invention comprises from 5 wt % to 50 wt % of copper oxide, weight percentage based on the total weight of the catalyst; more preferably, the catalyst comprises from 10 wt % to 50 wt % of copper oxide, weight percentage based on the total weight of the catalyst; even more preferably, the catalyst comprises from 10 wt % to 30 wt % of copper oxide, weight percentage based on the total weight of the catalyst.

In some aspects, the catalyst of the present invention further comprises a compound of at least one element selected from Fe, Co, Zn, Ni, Cr, Mn, Mg, Ba, and rare earth metals, such as Y, Nd, Pr, Sm, Gd, Ce, La, Er, Dy, and Ho. Said compound is notably an oxide of the element mentioned above. Preferably, the element is Mg. Such compound can notably function as promoter so as to further enhance the catalytic activities of the catalyst. The promoter may be a single compound or a mixture of compounds of more than one elements. Such promoter may be comprised from 0.1 wt % to 20 wt %, preferably from 0.5 wt % to 10 wt %, more preferably from 0.5 wt % to 5 wt %, based on the total weight of the catalyst.

Without wishing to be bound by theory, it is believed that the specific porosity of the catalyst exhibits a high cycle time in the catalysis. The presence of copper oxide, and optionally the promoter as well, at the surface of the pores of the porous alumina makes it possible to have a better catalytic effect than that with the catalyst in unsupported, bulk form.

Generally, the porous alumina of the invention is obtained by dehydration of gibbsite, of bayerite, of nordstrandite or of their various mixtures. Reference may be made, for example, to the Kirk-Othmer encyclopedia, volume 2, pages 291-297.

The porous alumina used in the present invention can be prepared by bringing a hydrated alumina, in finely divided form, into contact with a hot gas stream at a temperature of between 400° C. and 1000° C., then keeping the hydrate and the gases in contact for a period ranging from a fraction of a second up to 10 seconds and finally separating the partially dehydrated alumina and the hot gases. Reference may in particular be made to the process described in U.S. Pat. No. 2,915,365.

It is also possible to carry out the autoclaving of agglomerates of the alumina obtained above, in aqueous medium, optionally in the presence of acid, at a temperature greater than 100° C., and preferably of between 150° C. and 250° C., for a period preferably of between 1 and 20 hours, then to dry them and to calcine them.

The calcination temperature is adjusted so that specific surface area and pore volumes situated within the ranges of values indicated above are obtained.

Due to their main manufacturing processes, the porous alumina used in the present process most often contain sodium, the content of which is usually expressed as weight of $Na_2O$ with respect to the weight of the alumina.

The catalyst can be used in various forms, such as powder, balls, crushed material, extrudates or pellets, it optionally being possible for the shaping to be carried out using a binder.

It can first of all be alumina balls resulting from an oil-drop shaping (or coagulation as drops). This type of ball can, for example, be prepared by a process according to the teaching of Patents EP-A-0,015,801 or EP-A-0,097,539. Control of the porosity can be carried out, in particular, according to the process described in Patent EP-A-0,097,539, by coagulation as drops of an aqueous alumina suspension or dispersion or of a solution of a basic aluminium salt which is provided in the form of an emulsion composed of an organic phase, of an aqueous phase and of a surfactant or of an emulsifier. The said organic phase can, in particular, be a hydrocarbon.

It can also be crushed alumina materials. These crushed materials can be the result of the crushing of any type of alumina-based material such as, for example, balls obtained by all types of process (oil-drop, bowl granulator or rotating drum) or extrudates. Control of the porosity of these crushed materials is achieved by the choice of the alumina-based material which is crushed in order to produce them.

It can also be alumina extrudates. The latter can be obtained by kneading and then extruding an alumina-based material, it being possible for the said material to result from the rapid dehydration of hydrargillite or from the precipitation of an alumina gel. Control of the porosity of these extrudates can be achieved by the choice of the alumina used and by the preparation conditions for this alumina or by the kneading conditions for this alumina before extrusion. The alumina can thus be mixed during kneading with pore-forming agents. The extrudates can, by way of example, be prepared by the process described in U.S. Pat. No. 3,856,708.

According to the invention, the catalyst which comprises the catalytic metal(s) supported on the porous alumina, can be obtained generally by impregnation of the porous alumina support, with a solution of a salt or compounds of the elements mentioned above, and are then dried and calcined at a temperature greater than or equal to 400° C., in order optionally and advantageously to convert the said compounds or salts into oxygenated compounds, preferably into oxides.

In order to carry out the process of the invention, the reactant aliphatic alcohol and the reactant aminating agent are mixed according to a desired molar ratio. The reactant mixture is preferably mixed together with a flow of hydrogen. The mixture may be preheated to 200-400° C. Then the mixture may be continuously introduced into a reaction zone. The molar ratio of the aliphatic alcohol to the aminating agent may be in the range of from 1:1 to 1:2, preferably, in the range of from 1:1 to 1:1.5, more preferably, in the range of from 1:1 to 1:1.2. The molar ratio of the aliphatic alcohol to the hydrogen may be in the range of from 1:5 to 1:20, preferably in the range of from 1:10 to 1:18, more preferably in the range of from 1:10 to 1:15. Alternatively, an inert gas, such as nitrogen, can be added into the reactant mixture and introduced into the reaction zone.

Preferably, the process of the invention is a gas phase reaction. In such case, the reactant mixture is introduced into the reaction zone in vapour phase, at a liquid hourly space velocity (volume of liquid alcohol per volume of catalyst per hour) of from 0.05 to 5.0 kg of alcohol per kg of catalyst per hour, preferably from 0.1 to 2.0 kg of alcohol per kg of catalyst per hour, more preferably, from 0.5 to 1 kg of alcohol per kg of catalyst per hour.

The reaction is preferably carried out over a fixed bed wherein the catalyst according to the present invention is loaded. It is appreciated that the reaction may also be carried out in a stirring vessel which can be heated and which is provided with a device for the circulation of the reactant mixture. In such case, the reactants and the catalyst can be loaded into the vessel before the reaction is initiated. Accordingly, in another aspect of the present invention, there is provided a composition, notably a reaction system, comprising:

an aliphatic alcohol of formula (I)

$$R_1CH_2OH \qquad (I),$$

wherein $R_1$ is a linear or branched, saturated or unsaturated aliphatic group having from 3 to 21 carbon atoms;

an aminating agent of formula (II)

wherein $R_2$ and $R_3$, the same or different, are hydrogen or a linear or branched, saturated or unsaturated aliphatic group having from 1 to 24 carbon atoms; and a catalyst comprising copper oxide on a support made of porous alumina; wherein the porous alumina has a volume, corresponding to pores greater than 500 Å in diameter, of from 10 ml/100 g to 95 ml/100 g.

The temperature of the reaction may be in the range of from 150° C. to 350° C., preferably, in the range of from 200° C. to 300° C., more preferably, in the range of from 200° C. to 250° C. The pressure in the reaction zone may be in the range of 0 to 5 barg, preferably in the range of 0 to 2 barg, more preferably, in the range of from 0 to 1 barg, even more preferably, in the range of from 0 to 0.5 barg.

The reaction may be stopped by shutting down the input stream into the reactor. After the reaction has completed, the reaction product in the reaction zone may be subject to further steps such as distillation, condensation and recycling, by using procedures which are well known by a person skilled in the art, so as to recover the desired products. In one embodiment, the effluent in the reaction zone which containing the desired alkyl dimethylamine product is passed through a condenser to cool the reaction product to 30 to 150° C. Hydrogen, unreacted dimethylamine, water and small amount of monomethylamine and trimethylamine by products are removed overhead. The condensed liquid product is then sent to a distillation stage, wherein the desired alkyldimethylamine product is separated from heavier products, such as dialkyl methylamines.

It is appreciated that the process of the present invention may employ a single fixed bed reactor or multiple fixed bed reactors. In the latter case, for example, the process may employs two fixed bed reactors, wherein the reaction product in the first fixed bed reactor is introduced into the second fixed bed reactor together with a fresh stream of the aminating agent. The conditions in the second fixed bed reactor may be substantially same as those in the first fixed bed reactor as described above. Preferably, the reaction temperature in the second fixed bed reactor is 5-30° C. lower than that in the first fixed bed reactor.

EXAMPLES

Various catalysts, which comprise copper oxide (or copper oxide and magnesium oxide) on porous alumina support were prepared by impregnating porous alumina beads with aqueous solutions of soluble salts of copper and/or magnesium. The porous alumina beads used had been described in U.S. Pat. No. 6,262,259. The volume corresponding to pores of diameter above 500 Å, and the specific surface areas as well, of the porous alumina are shown in Table 1 below. For preparing catalysts containing copper, the porous alumina beads were impregnated with an aqueous solution of $Cu(NO_3)_2/2.5H_2O$ having appropriate concentration. Then the beads were dried in an oven at 120° C. for 4 hours and calcinated at 500° C. for 2 hours with a temperature ramp of 1° C./min. For preparing catalysts containing copper and magnesium, porous alumina beads were firstly impregnated with copper solution as described above. Then the beads were impregnated with an aqueous solution of $Mg(NO_3)_2/6H_2O$ having appropriate concentration. Then the beads were dried in an oven at 120° C. for 4 hours and calcinated at 500° C. for 2 hours with a temperature ramp of 1° C./min.

The components of the catalysts used and the porosity of the porous alumina used are shown in Table 1 below (Specific Surface Area=SS; Total Pore Volume=TPV; volume for the pores with a diameter greater than 70 Å=V70 Å; volume for the pores with a diameter greater than 500 Å=V500 Å; the weight percentages of CuO and MgO is based on the total weight of the catalyst).

TABLE 1

| # | Alumina | SS (m²/g) | TPV (ml/100 g) | V70 Å (ml/100 g) | V500 Å (ml/100 g) | CuO (mass %) | MgO (mass %) |
|---|---------|-----------|----------------|------------------|-------------------|--------------|--------------|
| 1 | A1 | 139 | 117 | 116 | 50 | 20 | 0 |
| 2 | A1 | 139 | 117 | 116 | 50 | 20 | 0.5 |

TABLE 1-continued

| # | Alumina | SS (m²/g) | TPV (ml/100 g) | V70 Å (ml/100 g) | V500 Å (ml/100 g) | CuO (mass %) | MgO (mass %) |
|---|---------|-----------|----------------|------------------|-------------------|--------------|--------------|
| 3 | A2 | 408 | 37 | 14 | 7 | 20 | 0 |
| 4 | A2 | 408 | 37 | 14 | 7 | 20 | 0.5 |
| 5 | A3 | 352 | 43 | 17 | 8 | 20 | 0 |
| 6 | A3 | 352 | 43 | 17 | 8 | 20 | 0.5 |

In order to investigate the catalytic behaviours of the above mentioned catalysts, the catalysts were loaded into a tubular fixed bed reactor (2 inch diameter and 1 meter length), respectively. Then, a mixture of dodecyl alcohol and dimethylamine, together with a flow of hydrogen gas were heated through a gasifier at 215° C. The molar ratio of the alcohol/dimethylamine/hydrogen was 1:1.2:14.7. Then the preheated mixture, which was in vapor phase, was introduced into the fixed bed reactor loaded with the catalyst, at a feeding rate of 0.5 kg of alcohol per kg of catalyst per hour. The reaction temperature in the fixed bed reactor was set at 215° C. and the pressure was set at 0.2 barg. The product stream from an outlet of the fixed bed reactor was cooled down to ambient temperature through a heat exchanger and samples of the product stream were collected for analysis. The samples collected were subject to gas chromatograph analysis. The conversion rate of the alcohol (DC) and the selectivity of the desired tertiary amine were determined according to below:

Conversion rate of the alcohol (DC)=(total moles of alcohol inputted−total moles of unreacted alcohol in the product mixture)/total moles of alcohol inputted Selectivity of the tertiary amine=total moles of tertiary amine in the product mixture/(total moles of alcohol inputted−total moles of unreacted alcohol in the product mixture)

Results are shown in Table 2 below:

TABLE 2

| # | DC of Alcohol (%) | Selectivity of Tertiary Amine (%) |
|---|-------------------|-----------------------------------|
| 1 | 98 | 96 |
| 2 | 97 | 96 |
| 3 | 87 | 90 |
| 4 | 82 | 93 |
| 5 | 80 | 91 |
| 6 | 79 | 89 |

It was shown that the catalysts supported on the porous alumina according to the present invention (having a V500 Å value of above 10 ml/100 g) exhibited markedly higher conversion rate of alcohol and markedly higher selectivity of tertiary amine compared with those with support having a V500 Å value of below 10 ml/100 g.

The invention claimed is:
1. A process, comprising reacting an aliphatic alcohol of formula (I)

$$R_1CH_2OH \quad (I),$$

wherein $R_1$ is a linear or branched, saturated or unsaturated aliphatic group having from 3 to 21 carbon atoms, with an aminating agent of formula (II)

(II)

wherein $R_2$ and $R_3$, the same or different, are hydrogen or a linear or branched, saturated or unsaturated aliphatic group having from 1 to 24 carbon atoms, for obtaining an aliphatic amine of formula (III), (IV) or (V)

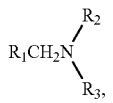
(III)

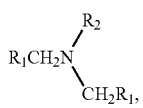
(IV)

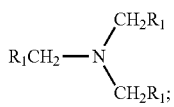
(V)

wherein the reaction is carried out in the presence of a catalyst, wherein the catalyst comprises from 5 wt % to 50 wt % of copper oxide; optionally from 0.1 wt % to 20 wt % of a compound of at least one element selected from Fe, Co, Zn, Ni, Cr, Mn, Mg, Ba and rare earth metals; the balance being a support made of porous alumina, weight percentage based on the total weight of the catalyst; wherein the porous alumina has a volume, corresponding to pores greater than 500 Å in diameter, of from greater than 30 ml/100 g to 95 ml/g, as determined by mercury porosimetry.

2. The process according to claim 1, wherein the porous alumina has a specific surface area of from 10 m²/g to 280 m²/g.

3. The process according to claim 1, wherein the porous alumina has a specific surface area of from 50 m²/g to 280 m²/g.

4. The process according to claim 1, wherein the aminating agent has the formula (VI)

(VI)

wherein $R_4$ and $R_5$, the same or different, are a linear or branched, saturated or unsaturated aliphatic group having from 1 to 24 carbon atoms, the aliphatic amine has the formula (VII):

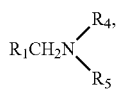
(VII)

wherein $R_1$ is a linear or branched, saturated or unsaturated aliphatic group having from 3 to 21 carbon atoms, $R_4$ and $R_5$ are as defined in formula (VI).

5. The process according to claim 1, wherein the aliphatic alcohol and the aminating agent are mixed together with a flow of hydrogen and the mixture is continuously introduced into a reaction zone, wherein the molar ratio of the aliphatic alcohol/the aminating agent/the hydrogen is in the range of from 1:1:5 to 1:2:20.

6. The process according to claim 5, wherein the molar ratio of the aliphatic alcohol/the aminating agent/the hydrogen is in the range of from 1:1:5 to 1:1.2:15.

7. The process according to claim 1, wherein the reaction is carried out at a temperature of from 150° C. to 350° C.

8. The process according to claim 1, wherein the reaction is carried out at a temperature of from 2° C. to 250° C.

9. The process according to claim 1, wherein the reaction is carried out under a pressure of from 0 to 5 barg.

10. The process according to claim 1, wherein the reaction is carried out under a pressure of from 0 to 0.5 barg.

* * * * *

UNITED STATES PATENT AND TRADEMARK OFFICE
CERTIFICATE OF CORRECTION

PATENT NO. : 11,084,776 B2
APPLICATION NO. : 16/074556
DATED : August 10, 2021
INVENTOR(S) : Shengyin Ye et al.

Page 1 of 1

It is certified that error appears in the above-identified patent and that said Letters Patent is hereby corrected as shown below:

In the Claims

At Column 11, Claim 1, Line 37, "95 ml/g" should read -- 95 ml/100 g --.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*